(12) United States Patent
Baik et al.

(10) Patent No.: US 11,058,589 B2
(45) Date of Patent: Jul. 13, 2021

(54) SURGICAL SPONGE

(71) Applicant: Generations International Asset Management Company LLC, St. Thomas, VI (US)

(72) Inventors: Peter Baik, Tulsa, OK (US); Courtney Craft, Knoxville, TN (US); Michael Kastura, Knoxville, TN (US); Ethan Edward Valentine, Knoxville, TN (US)

(73) Assignee: INTERNATIONAL PRIVATE BANK LLC, St. Thomas, VI (US)

( * ) Notice: Subject to any disclaimer, the term of this patent is extended or adjusted under 35 U.S.C. 154(b) by 231 days.

(21) Appl. No.: 16/209,394

(22) Filed: Dec. 4, 2018

(65) Prior Publication Data

US 2019/0358092 A1  Nov. 28, 2019

Related U.S. Application Data

(63) Continuation-in-part of application No. 29/670,304, filed on Nov. 15, 2018, and a continuation-in-part of application No. 15/989,586, filed on May 25, 2018.

(51) Int. Cl.
| | |
|---|---|
| *A61F 13/36* | (2006.01) |
| *A61F 13/45* | (2006.01) |
| *A61F 13/15* | (2006.01) |
| *A61F 13/20* | (2006.01) |
| *A61F 13/34* | (2006.01) |

(52) U.S. Cl.
CPC ........ *A61F 13/36* (2013.01); *A61F 13/15707* (2013.01); *A61F 13/45* (2013.01); *A61F 13/2022* (2013.01); *A61F 13/34* (2013.01); *A61F 2013/15373* (2013.01)

(58) Field of Classification Search
CPC .... A61F 13/36; A61F 13/15707; A61F 13/45; A61F 13/15203; A61F 13/00008; A61F 13/2022; A61F 2013/15373; A61F 13/2068; A61F 13/2057; A61F 13/2054; A61F 2013/4506–4593; A61B 2050/375
See application file for complete search history.

(56) References Cited

U.S. PATENT DOCUMENTS

| | | |
|---|---|---|
| 1,985,667 A | 12/1934 | Nelson et al. |
| 2,972,350 A | 2/1961 | Marta |

(Continued)

OTHER PUBLICATIONS

Gholami SS, Shekarriz B, Rudnick D, Duh QY, Stoller ML, Kittner Roll Gauze Sponge for Laproscopic, Robotic Procedure, Da Vinci Surgery, The Laproscopic Sponge from National Center for Biotechnology Information (NCBI), Dept. of Urology, University of California, San Francisco, CA 94143 United States of America, 3 pages, Date: 00/00/2012.

(Continued)

*Primary Examiner* — Susan S Su
(74) *Attorney, Agent, or Firm* — Luedeka Neely Group, PC (57) ABSTRACT

A surgical sponge including sponge material configured in an elongate sponge having at least two layers and a flattened shape characterized by a generally flat upper surface, a generally flat lower surface. The sponge has a thickness that is substantially less than a width of the sponge, a reduced dimension end of the elongate sponge having an end length and reducing in dimension distally along the end length. Stitches are located along the length of the sponge to maintain the flattened shape of the sponge.

14 Claims, 8 Drawing Sheets

(56) References Cited

U.S. PATENT DOCUMENTS

| | | | |
|---|---|---|---|
| 3,118,163 A | | 1/1964 | Rippen |
| 3,628,534 A | * | 12/1971 | Donohue ................ A61L 15/60 |
| | | | 604/366 |
| 3,710,793 A | * | 1/1973 | Glassman ........... A61F 13/2068 |
| | | | 604/359 |
| 3,834,390 A | | 9/1974 | Hirsch |
| 4,071,955 A | * | 2/1978 | Julius .................. A61F 13/2008 |
| | | | 433/136 |
| 4,477,256 A | | 10/1984 | Hirsch |
| 5,112,325 A | * | 5/1992 | Zachry .................... A61F 13/44 |
| | | | 604/362 |
| 5,725,517 A | | 3/1998 | DeBusk |
| 6,186,994 B1 | * | 2/2001 | Bowles ............... A61F 13/2068 |
| | | | 604/385.17 |
| 2012/0101462 A1 | * | 4/2012 | Lee ....................... A61F 13/206 |
| | | | 604/379 |
| 2012/0259302 A1 | * | 10/2012 | Chaisumdet ............ A61F 13/36 |
| | | | 604/367 |
| 2012/0283684 A1 | * | 11/2012 | Schmidt-Foerst .......................... |
| | | | A61F 13/2062 |
| | | | 604/385.17 |
| 2012/0283762 A1 | * | 11/2012 | Shao ................. A61F 13/00063 |
| | | | 606/180 |
| 2013/0079590 A1 | | 3/2013 | Bengtson |
| 2014/0088529 A1 | * | 3/2014 | Bengtson ................ A61F 13/36 |
| | | | 604/360 |
| 2015/0038929 A1 | * | 2/2015 | Van Malderen ...... A61F 13/539 |
| | | | 604/370 |
| 2016/0015572 A1 | * | 1/2016 | Viens ................ A61F 13/15577 |
| | | | 604/385.18 |
| 2016/0367409 A1 | * | 12/2016 | Chen ....................... A61F 13/84 |
| 2018/0333309 A1 | * | 11/2018 | Merritt .................. A61B 90/98 |

OTHER PUBLICATIONS

International Searching Authority, PCT/US19/ 17577, date of mailing May 6, 2019, International Search Report and Written Opinion.

* cited by examiner

SURGICAL SPONGE

CROSS-REFERENCE TO RELATED APPLICATION

This application is a continuation-in-part of co-pending U.S. application Ser. No. 15/989,586 filed May 25, 2018, and entitled SURGICAL SPONGE, and is a continuation-in-part of co-pending U.S. Design application Ser. No. 29/670,304 filed Nov. 15, 2018, and entitled SURGICAL SPONGE each incorporated herein by reference in its entirety.

FIELD

This disclosure relates to surgical sponges. More particularly, this disclosure relates to improved surgical sponges having enhanced structure and function.

BACKGROUND

Improvement is desired in the construction of surgical sponges. Conventional surgical sponges have various shortcomings. For example, better absorption of surgical fluids is desired. Also, conventional sponges often do not stay intact when wet, are cumbersome and get tangled with surgical instruments, and are difficult to deploy and retrieve through cannulas and the like associated with laparoscopic surgery.

The present disclosure advantageously provides improved surgical sponges that overcome many of the shortcomings of conventional sponges.

SUMMARY

The above and other needs are met by surgical sponges and methods for making surgical sponges according to the disclosure.

In one aspect, a surgical sponge includes sponge material configured in an elongate sponge having at least two layers and a flattened shape characterized by a generally flat upper surface, a generally flat lower surface, with the sponge having a thickness that is substantially less than a width of the sponge, a reduced dimension end of the elongate sponge having an end length and reducing in dimension distally along the end length; and stitches along the length of the sponge to maintain the flattened shape of the sponge.

In another aspect, a sponge materially includes a single sheet sponge material configured in an elongate sponge having two layers and a flattened shape characterized by a generally flat upper surface, a generally flat lower surface, with the sponge having a thickness that is substantially less than a width of the sponge. The ratio of the width of the sponge to the thickness of the sponge is at least about 5 to 1. Stitches are provided in a linear pattern proximate a longitudinal centerline of the sponge to maintain the flattened shape of the sponge.

In accordance with a further aspect, there is provided a method for making a surgical sponge. The method includes the steps of providing a sponge material and configuring the sponge material in an elongate shape having at least two layers and a flattened shape characterized by a generally flat upper surface, a generally flat lower surface. The sponge has a thickness that is substantially less than a width of the sponge, a reduced dimension end of the elongate sponge having an end length and reducing in dimension distally along the end length. Stitches are provided stitches along the length of the sponge to maintain the flattened shape of the sponge.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1A:
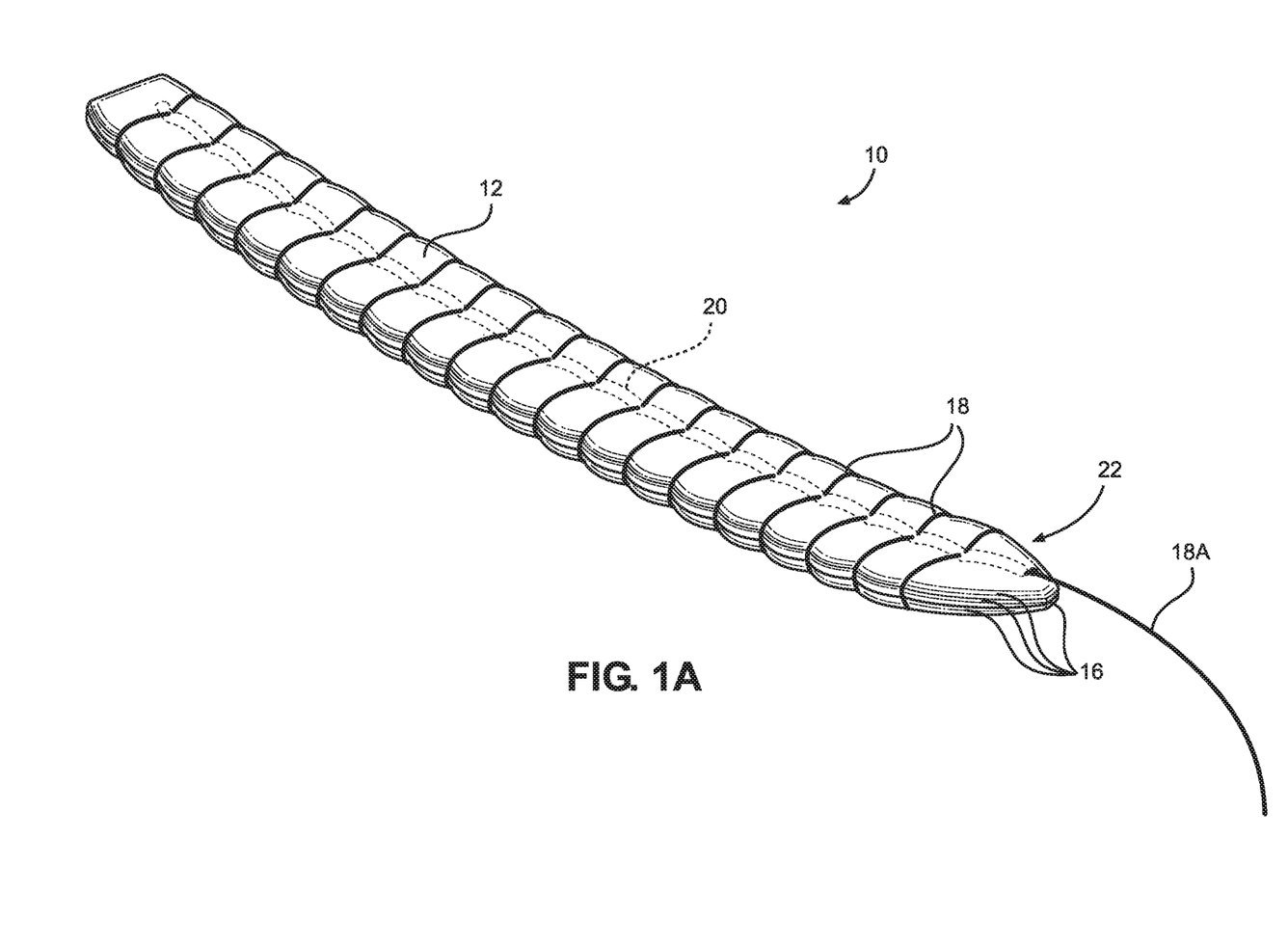
FIG. 1A is a perspective view of a surgical sponge according to the disclosure.
Figure 1B:
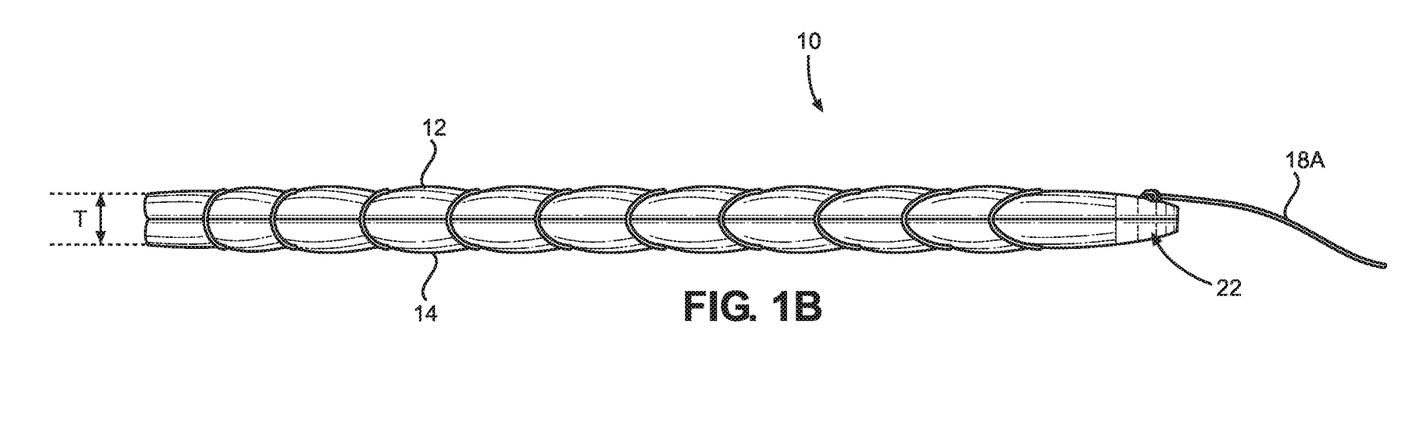
FIG. 1B is a right side view of the surgical sponge of FIG. 1A.
Figure 1C:
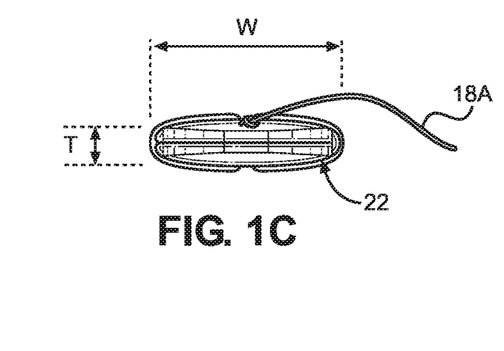
FIG. 1C is a front end view of the surgical sponge of FIG. 1A.

With initial reference to FIGS. 1A-1C, there is shown a surgical sponge 10 according to the disclosure. The sponge 10 is particularly configured for use with laparoscopic, thorascopic, and robotic surgical procedures and equipment. The appearance of the sponge 10 is also configured to be aesthetically pleasing and includes various ornamental aspects and features.

As shown, the sponge 10 is elongate, but has a flattened or non-cylindrical cross-section characterized by a generally flat upper surface 12, a generally flat lower surface 14, with the sponge 10 having a thickness T that is substantially less than a width W of the sponge 10 to facilitate passage of the sponge 10 through a cannula or the like. In a preferred embodiment, the ratio of the width of the sponge to its thickness is at least about 2 to 1.

The sponge 10 is constructed to have multiple compressed layers 16. For example, at least about four layers is preferred. To accomplish this, a single piece of sponge material is rolled or folded or multiple pieces of sponge material are utilized, with stitches 18 being applied along the length of the sponge 10 to compress the sponge material and maintain the layers in compression to yield the elongate flattened shape as depicted. It has been observed that the structure of the sponge 10 has improved absorbency as compared to conventional sponge structures that do not provide compressed layers held in compression, and the sponge 10 remains intact when wet.

A preferred sponge material is a sterile rayon fiber neuro sponge material available from DeRoyal Industries of Powell, Tenn. The sponge material preferably includes an integrated x-ray detectable strip 20. The stitches 18 are desirably formed as locking stitches and formed using 0-silk suture material. The stitches 18 aid in retaining the dimensions of the sponge 10 when saturated. For example, the sponge will tend to swell as its intake of fluids increases, causing the material of the sponge to swell or expand. Absent the stitches 18, the sponge 10 would swell undesirably and potentially render the sponge of dimensions unsuitable for being retrieved through a trocar. The stitches 18 serve to inhibit the swelling of the sponge so that the sponge when saturated may be retrieved through a trocar. The stitches 18 also tend to maintain the sponge structure, as the sponge material is more vulnerable to tearing and the like when wet.

Figure 2A:
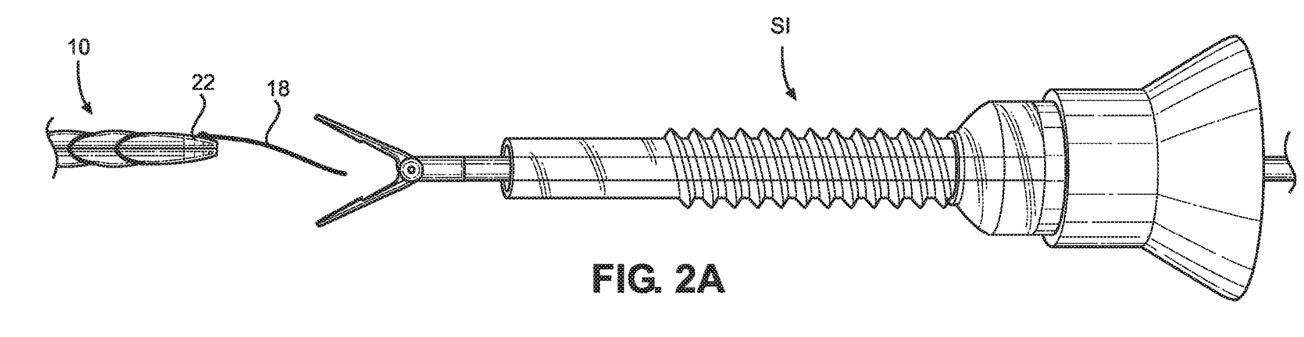
FIGS. 2A-2C show retrieval of the surgical sponge of FIG. 1 during a surgical procedure.
Figure 2B:
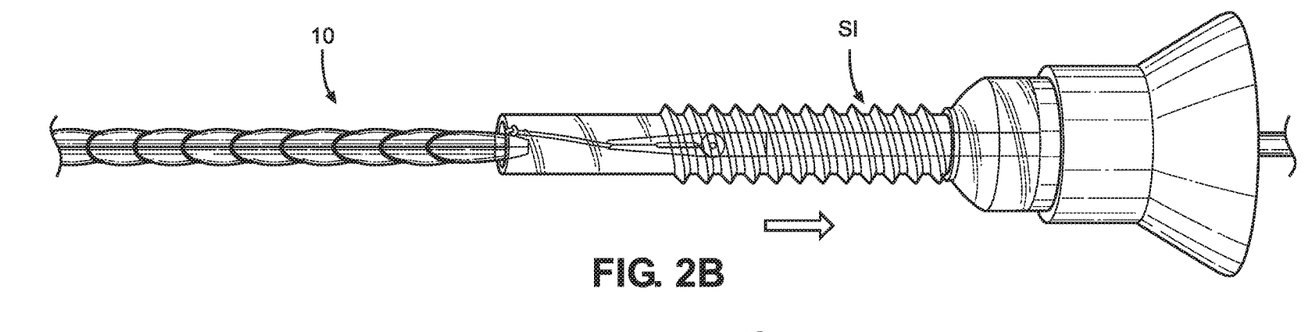
Figure 2C:
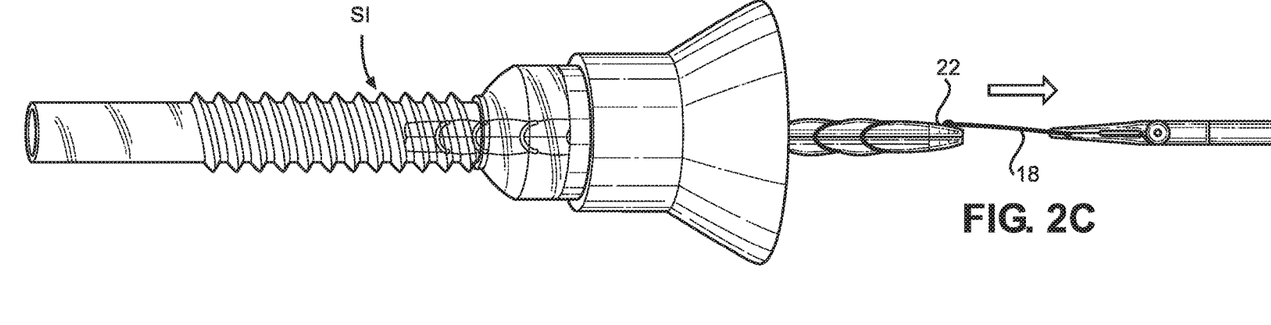

A length 18a of the stitch material is left to extend from at least one end 22 of sponge 10 to provide a structure that is engageable by the surgeon for use in positioning or removal of the sponge 10. In this regard, at least the end 22 of the sponge 10 having the length 18a of stitch material is angled, tapered, pointed or the like to provide a shape that reduces in dimension along its length distally. The end 22 is thus configured to be more easily guided into a trocar or the like for deployment and retrieval. For example, as seen in FIGS. 2A-2C, the length 18a of the stitch material, the flattened shape of the sponge 10, and the reduced dimensioned end 22 enable the sponge 10 to be more easily retrieved and guided into and through a trocar of laparoscopic or other surgical instrument SI.

Figure 3A:
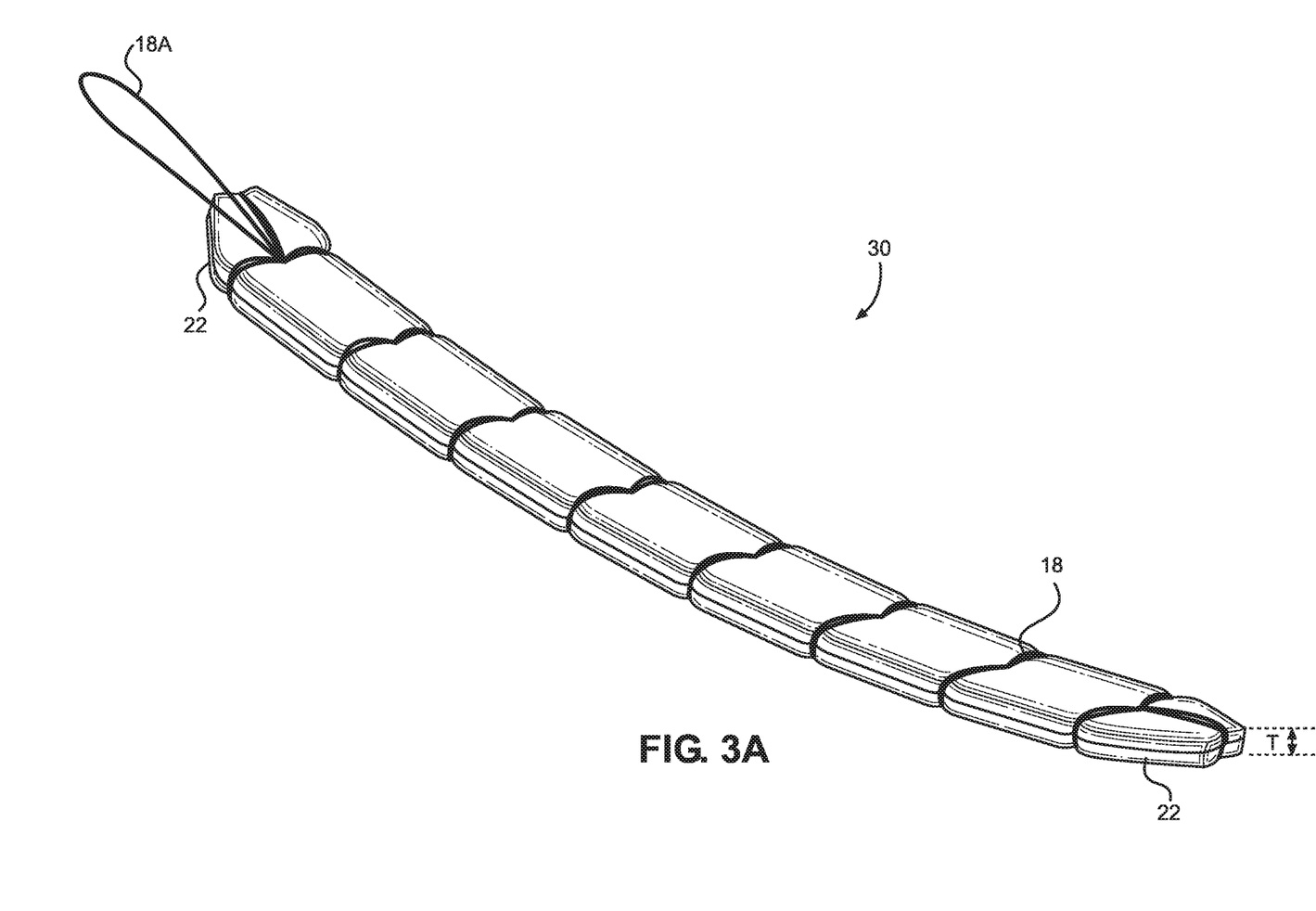
FIGS. 3A-3C show an alternate embodiment of a surgical sponge according to the disclosure.
Figure 3B:
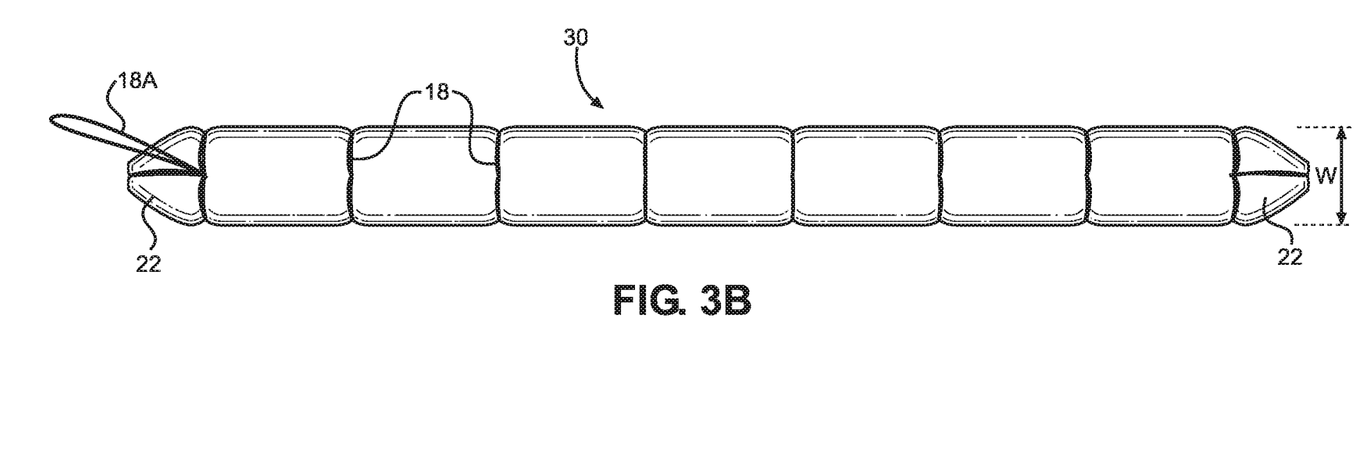
Figure 3C:
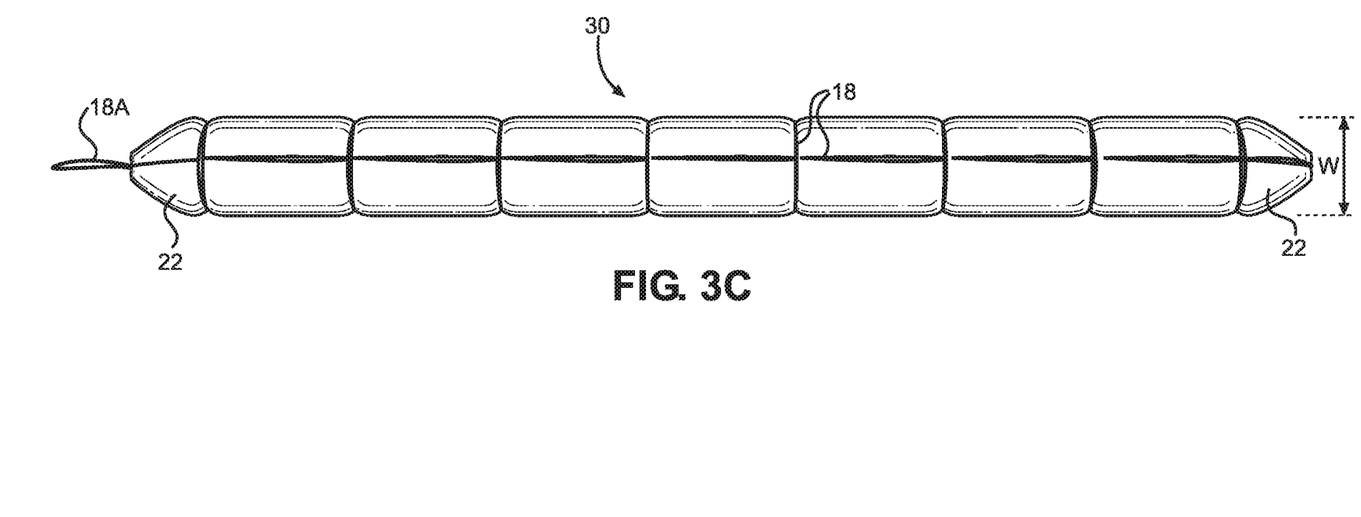

With reference to FIGS. 3A-3C, there is shown another embodiment of a sponge 30. The sponge 30 is substantially identical to the sponge 10 and uses the same reference characters. However, stitches 18 of the sponge 30 are configured in a pattern that is more easily accomplished using automated stitching equipment. Also, each end of the sponge 30 has a reduced dimensioned end 22, and the length 18a of the stitch material is configured as a loop to facilitate grasping thereof. The appearance of the sponge 30 is also configured to be aesthetically pleasing and includes various ornamental aspects and features.

Figure 4A:
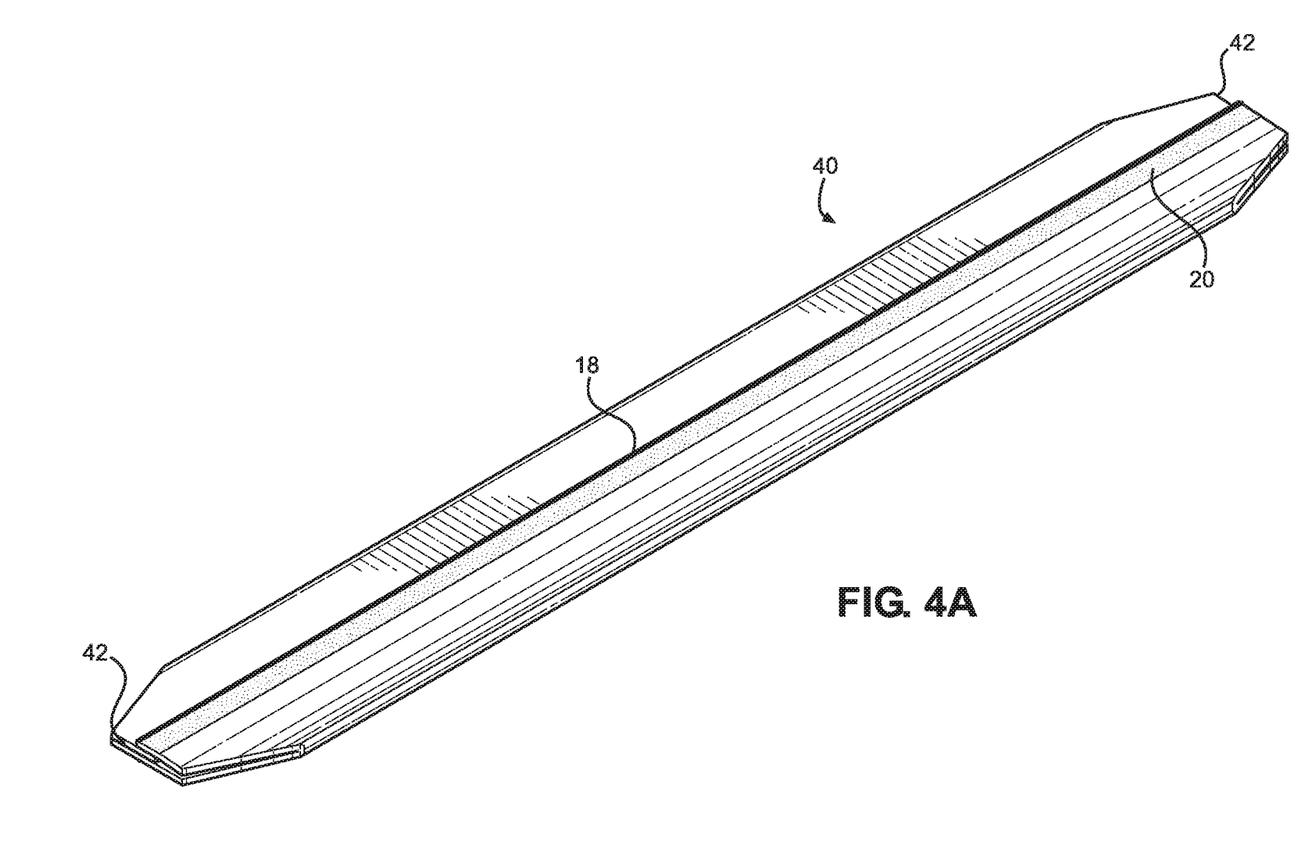
FIGS. 4A-4F show yet another embodiment of a surgical sponge according to the disclosure.
Figures 4B, 4C:
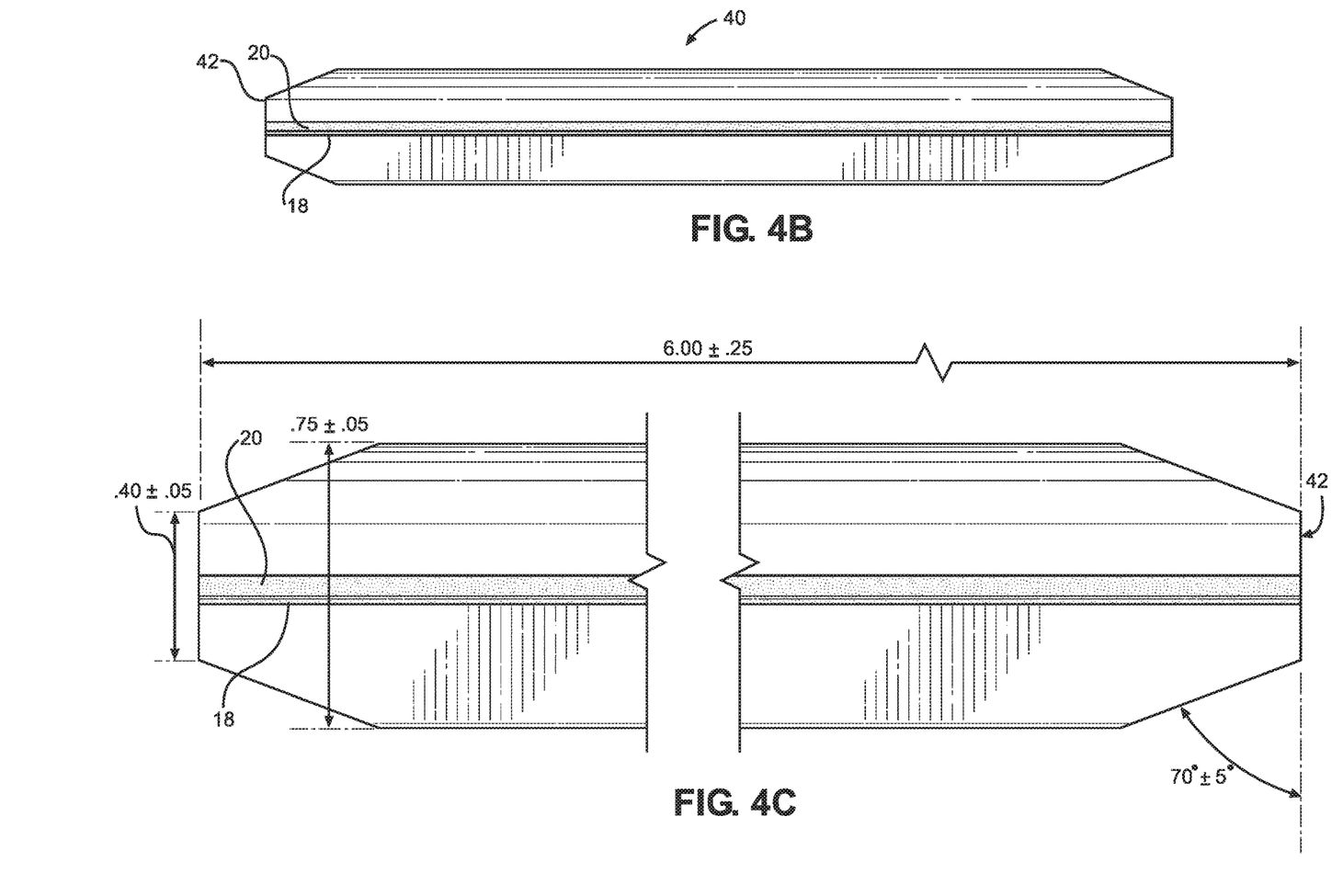
Figure 4D:
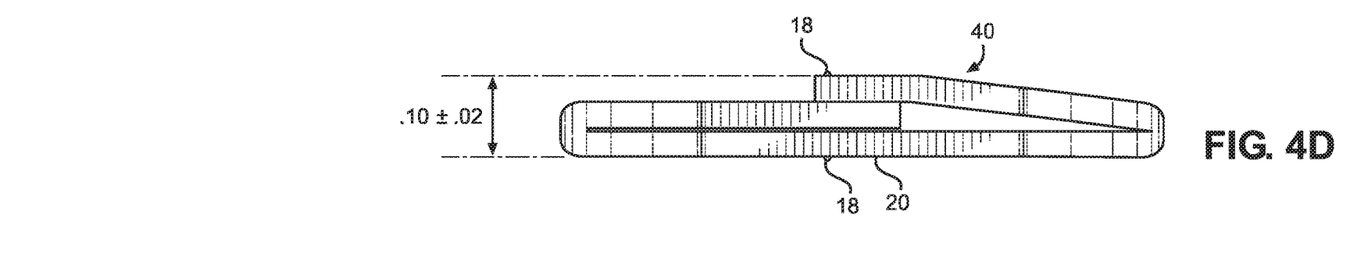
Figure 4E:
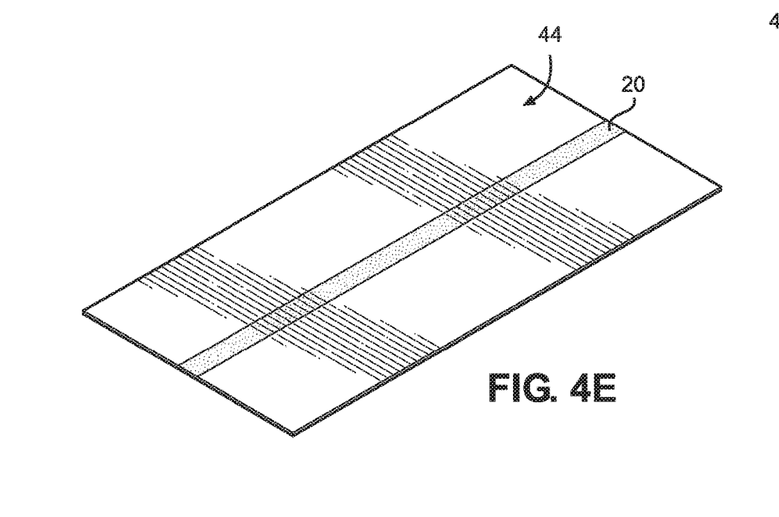
Figure 4F:
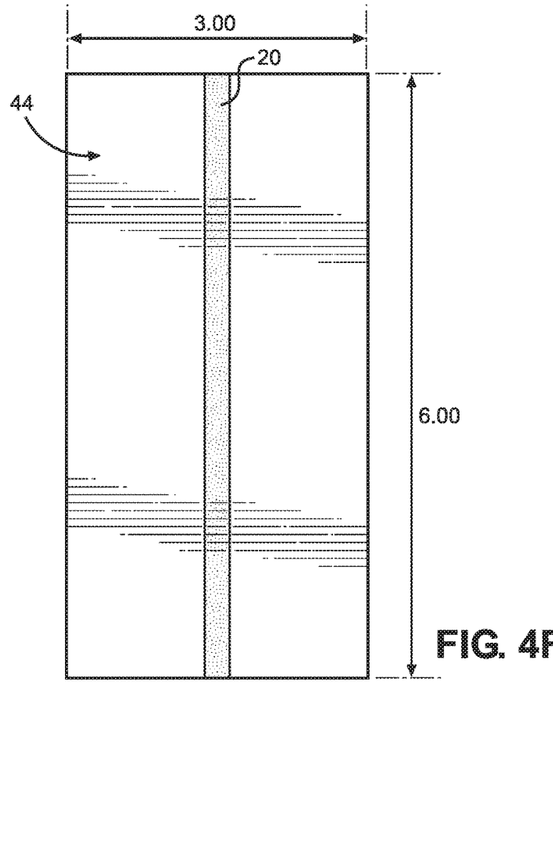

With reference to FIGS. 4A-4F, there is shown another embodiment of a sponge 40. The sponge 40 is similar to the sponges 10 and uses the same reference characters, except as noted hereafter. In addition, the stitches 18 of the sponge 40 are shown provided in a linear pattern proximate the longitudinal centerline of the sponge 40 that is easily accomplished using automated stitching equipment. Also, each end of the sponge 40 has a flat, tapered end 42. Further, the sponge 40 is of simplified construction and has a reduced thickness and a higher width to thickness ratio, with two layers at the edges and the central portion of the sponge being three layers, as seen in FIG. 4D. While not shown, one or both of the ends 42 may have a length 18a of the stitch material to facilitate grasping thereof. A single piece of sponge material 44 shown in FIGS. 4D and 4F may be used to provide the sponge 40, folded and stitched as shown in FIG. 4D, and then trimmed to form the ends 42. The appearance of the sponge 40 is also configured to be aesthetically pleasing and includes various ornamental aspects and features.

With additional reference to FIGS. 4C and 4D, the sponge 40 has a width of from about 0.7 to about 0.8 inches, and a thickness of from about 0.08 to about 0.12 inches. Thus, the ratio of the width of the sponge 40 to the thickness of the sponge 40 ranges from about 10 to about 5.8. Thus, allowing for minor variations, the ratio of the width to the thickness is at least about 5 to 1.

As will also be observed, the tapered ends 42 have a thickness that is the same as the thickness of the sponge 40 (from about 0.8 to about 0.12 inches), but a width of from about 0.35 to about 0.45 inches. Thus, the ratio of the width of the ends 42 of the sponge 40 to the thickness of the sponge 40 ranges from about 5.6 to about 2.9. Thus, allowing for minor variations, the ratio of the width to the thickness is at least about 2.5 to 1.

Accordingly, it will be appreciated that surgical sponges according to the disclosure are configured for improved absorption of surgical fluids, to remain intact when wet, and less cumbersome and easier to deploy and retrieve.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A surgical sponge, comprising: sponge material configured in an elongate sponge having a length with at least two layers and a flattened shape characterized by a generally flat upper surface along the length of the sponge, a generally flat lower surface along the length of the sponge, with the sponge having a thickness that is substantially less than a width of the sponge, a reduced dimension end of the elongate sponge having an end length and reducing in dimension distally along the end length; and stitches along the length of the sponge to compress the sponge material and maintain the layers in compression when the sponge is saturated with fluids so as to inhibit swelling of the sponge and maintain the flattened shape of the sponge when the sponge is saturated with fluids, wherein a left longitudinal edge of one of the layers of the sponge overlies a right longitudinal edge of another layer of the sponge to provide overlapping edges and the stitches extend though the overlapping edges.

2. The sponge of claim 1, wherein the sponge material is a single sheet of sponge material.

3. The sponge of claim 1, wherein each end of the sponge is of reduced dimension.

4. The sponge of claim 1, wherein the stitches are provided in a linear pattern proximate a longitudinal centerline of the sponge.

5. The sponge of claim 1, wherein the ratio of the width of the sponge to the thickness of the sponge is at least about 5 to 1.

6. A surgical sponge, consisting essentially of:
a single sheet sponge material having two longitudinal edge portions, the single sheet sponge material being configured in an elongate sponge having a central portion formed by overlapping the two longitudinal edge potions and a flattened shape characterized by a generally flat upper surface, a generally flat lower surface, with the sponge having a thickness that is substantially less than a width of the sponge so that the ratio of the width of the sponge to the thickness of the sponge is at least about 5 to 1; and stitches provided in a linear pattern proximate a longitudinal centerline of the sponge to join the overlapping longitudinal edge portions in a thickness direction, thereby maintaining the flattened shape of the sponge.

7. The sponge of claim 6, wherein the sponge has a reduced dimension end having the same thickness as the sponge but with a width such that the width of the reduced dimension end to the thickness of the sponge to the thickness of the sponge is at least about 2.5 to 1.

8. A method for making a surgical sponge, comprising the steps of:

providing a sponge material and configuring the sponge material in an elongate shape having a length with at least two layers and a flattened shape characterized by a generally flat upper surface along the length of the sponge, a generally flat lower surface along the length of the sponge, the sponge having a thickness that is substantially less than a width of the sponge, a reduced dimension end of the elongate sponge having an end length and reducing in dimension distally along the end length; and providing stitches along the length of the sponge to maintain the flattened shape of the sponge with a left longitudinal edge of one of the layers of the sponge positioned to overly a right longitudinal edge of another layer of the sponge to provide overlapping edges with the stitches extending through the overlapping edges.

9. The method of claim 8, wherein the step of providing a sponge material comprises providing a single sheet of sponge material.

10. The method of claim 8, wherein the stitches are provided in a linear pattern proximate a longitudinal centerline of the sponge.

11. The method of claim 8, wherein the ratio of the width of the sponge to the thickness of the sponge is at least about 5 to 1.

12. The method of claim 8, wherein the sponge has a reduced dimension end having the same thickness as the sponge but with a width such that the width of the reduced dimension end to the thickness of the sponge to the thickness of the sponge is at least about 2.5 to 1.

13. A surgical sponge, comprising: sponge material configured in an elongate sponge having a length with at least two layers and a flattened shape characterized by a generally flat upper surface along the length of the sponge, a generally flat lower surface along the length of the sponge, with the sponge having a thickness that is substantially less than a width of the sponge, a reduced dimension end of the elongate sponge having an end length and reducing in dimension distally along the end length; and the layers being bonded together along the length of the sponge to compress the sponge material and maintain the layers in compression when the sponge is saturated with fluids so as to inhibit swelling of the sponge and maintain the flattened shape of the sponge when the sponge is saturated with fluids, wherein a left longitudinal edge of one of the layers of the sponge overlies a right longitudinal edge of another layer of the sponge to provide overlapping edges and the overlapping edges are bonded directly to each other.

14. The sponge of claim 13, wherein the overlapping edges are bonded together by stitches extending through the overlapping edges.

* * * * *